(12) United States Patent
Park et al.

(10) Patent No.: US 11,369,753 B2
(45) Date of Patent: Jun. 28, 2022

(54) DUAL NEEDLE SYRINGE FOR PREVENTING INFECTION

(71) Applicants: Jong-Eun Park, Seoul (KR); Ah Ri Song, Seoul (KR)

(72) Inventors: Jong-Eun Park, Seoul (KR); Ah Ri Song, Seoul (KR)

( * ) Notice: Subject to any disclaimer, the term of this patent is extended or adjusted under 35 U.S.C. 154(b) by 121 days.

(21) Appl. No.: 16/623,290

(22) PCT Filed: Jun. 11, 2018

(86) PCT No.: PCT/KR2018/006614
§ 371 (c)(1),
(2) Date: Dec. 16, 2019

(87) PCT Pub. No.: WO2018/230913
PCT Pub. Date: Dec. 20, 2018

(65) Prior Publication Data
US 2020/0179617 A1 Jun. 11, 2020

(30) Foreign Application Priority Data
Jun. 14, 2017 (KR) .......................... 10-2017-0075066

(51) Int. Cl.
*A61M 5/32* (2006.01)
*A61M 5/178* (2006.01)
(Continued)

(52) U.S. Cl.
CPC ........ *A61M 5/3297* (2013.01); *A61M 5/1782* (2013.01); *A61M 5/3145* (2013.01); *A61M 5/34* (2013.01); *A61M 2205/7545* (2013.01)

(58) Field of Classification Search
CPC .............. A61M 5/3295; A61M 5/3297; A61M 5/1782; A61M 5/3145; A61M 5/34; A61M 2005/3114; A61M 2005/3201; A61M 2005/3117; A61M 2005/3118; A61M 5/3298; A61J 1/2096; A61J 1/2003;
(Continued)

(56) References Cited

U.S. PATENT DOCUMENTS 5,584,819 A * 12/1996 Kopfer .................. A61M 39/04
604/239
2008/0097353 A1 4/2008 Carr

FOREIGN PATENT DOCUMENTS

| KR | 20140065137 | 5/2014 | |
| KR | 20150000577 | 1/2015 | |
| KR | 20150000577 A * | 1/2015 | .............. A61M 5/34 |

* cited by examiner

*Primary Examiner* — Kevin C Sirmons
*Assistant Examiner* — Leah J Swanson
(74) *Attorney, Agent, or Firm* — IPLA P.A.

(57) ABSTRACT

A dual-needle syringe capable of preventing infection, including: an infusion needle shaft (3) configured to aspirate a liquid from a drug container (30); an injection needle shaft (5) having a sharp point of one end inserted into a body, and the other end connected to the syringe (10), through which the liquid filled in the syringe (10) is injected into a body; a hub barrel (7) engaged to a barrel (15) of the syringe (10) to infuse the liquid, which is aspirated from the drug container (30) through the infusion needle shaft (3), into the syringe (10) through the injection needle shaft (5), the hub barrel having an infusion needle shaft hub (21) and an injection needle shaft hub (23) which can be separated from each other before the liquid is injected; and a filter (9) configured to filter foreign substances contained in the liquid.

1 Claim, 8 Drawing Sheets

(51) Int. Cl.
*A61M 5/31* (2006.01)
*A61M 5/34* (2006.01)
(58) Field of Classification Search
CPC ........ A61J 1/2006; A61J 1/201; A61J 1/2013; A61J 1/20
See application file for complete search history.

DUAL NEEDLE SYRINGE FOR PREVENTING INFECTION

BACKGROUND

The present invention relates to a dual-needle syringe capable of preventing infection, and more particularly, to a dual-needle syringe that can prevent a needle from being infected by providing two detachable needle shafts, and can effectively remove foreign substances contained in a liquid which may be generated in a process of aspirating the liquid from a drug container and administrating it into a body.

In general, a syringe is a medical appliance capable of infusing a liquid from a drug container, such as an ampoule or a vial, and administrating it into a body, for example, a skin of a patient. An open end of a cylinder of the syringe is fitted with a needle to administer the drug from the drug container into the body.

In case where the drug container is a glass ampoule, it is opened by snapping a frangible neck of the ampoule. The drug can become dangerously contaminated by glass particles resulting from breaking of the ampoule. Otherwise, in case of a vial, when the needle passes through a rubber lid of the vial, the inside of the needle is caught by rubber debris.

Figure 1:
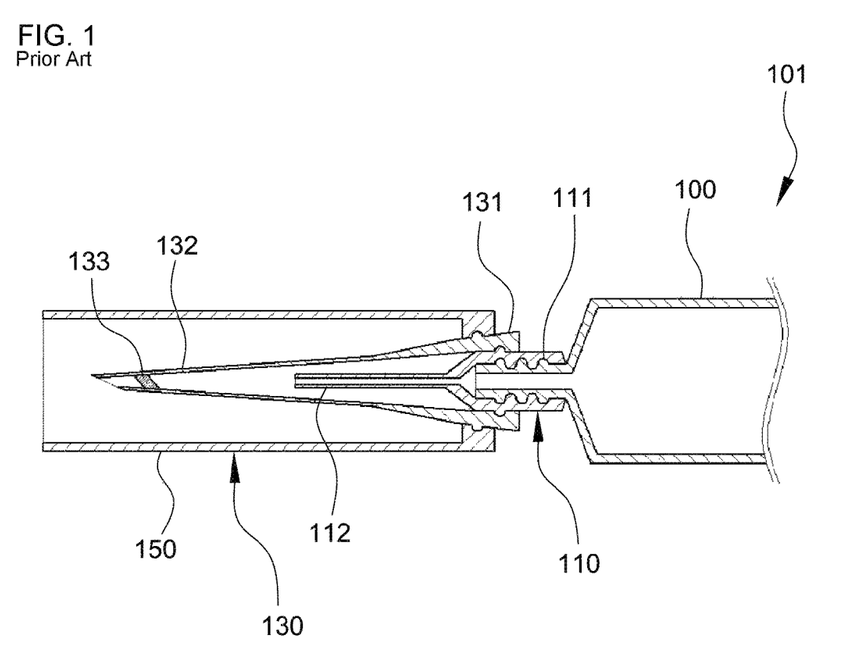
FIG. 1 is a cross-sectional view illustrating a syringe of the related art.

In order to solve the above drawbacks, as illustrated in FIG. 1, a syringe having a needle integrated with a filter has been proposed (e.g., Korean Patent No. 10-1435898).

The syringe of the related art, which is generally indicated by a reference numeral 101 in FIG. 1, includes an injection needle part 110, a filter needle part 130, and a filter needle protective cap 150. The injection needle part 110 has an injection needle hub 111 fastened to a syringe cylinder 100, and an injection needle 112 fastened to the injection needle hub 111, and the filter needle part 130 has a filter needle hub 131 fastened with the injection needle hub 111, a filter needle 132 communicating with the filter needle hub 131, and a filter 133 installed in an infusion space of the filter needle 132.

In order to aspirate a liquid into the cylinder 100 from a drug container, such as an ampoule or a vial, the protective cap 150 is opened, and then the filter needle 132 is inserted into the ampoule or vial. After that, a plunger is pulled to aspirate the liquid into the cylinder 100 from the drug container.

However, in case of the glass ampoule, since it is opened by snapping a frangible neck of the ampoule, the drug becomes dangerously contaminated by glass particles resulting from breaking of the ampoule. Otherwise, in case of the vial, when the needle passes through a rubber lid of the vial, the inside of the needle is caught by rubber debris. When the liquid is withdrawn from the drug container, various foreign substances are aspirated through the needle, as well as the liquid, but all foreign substances are filtered by the filter 133. Accordingly, in order to administrate a drug, the filter needle 132 is removed, and then the injection needle 112 is inserted into an affected part of a body.

The syringe 101 of the related art has a problem in that since the injection needle 112 and the filter needle 132 are disposed in the same direction and thus are overlapped with each other, the diameter of the filter needle 132 should be increased, and when the filter needle 132 is inserted into a rubber lid of a vial, resistance of the filter needle against the rubber lid is increased, so that the use thereof is not convenient.

Also, since the injection needle 112 extends from a front end of the cylinder 100 in a longitudinal direction, the injection needle 112 is not completely protected only by the filter needle 132, and thus the protective cap 150 is additionally provided. Therefore, the protective cap 150 should be removed in use which is an inconvenient process, and also a part is added to increase a cost thereof.

In addition, before the filter needle 132 is inserted into the drug container to aspirate the liquid into the syringe, the injection needle 112 should be positioned at a normal position in the filter needle 132 by adjusting the cylinder 100, which causes inconvenience in use.

Figure 2:
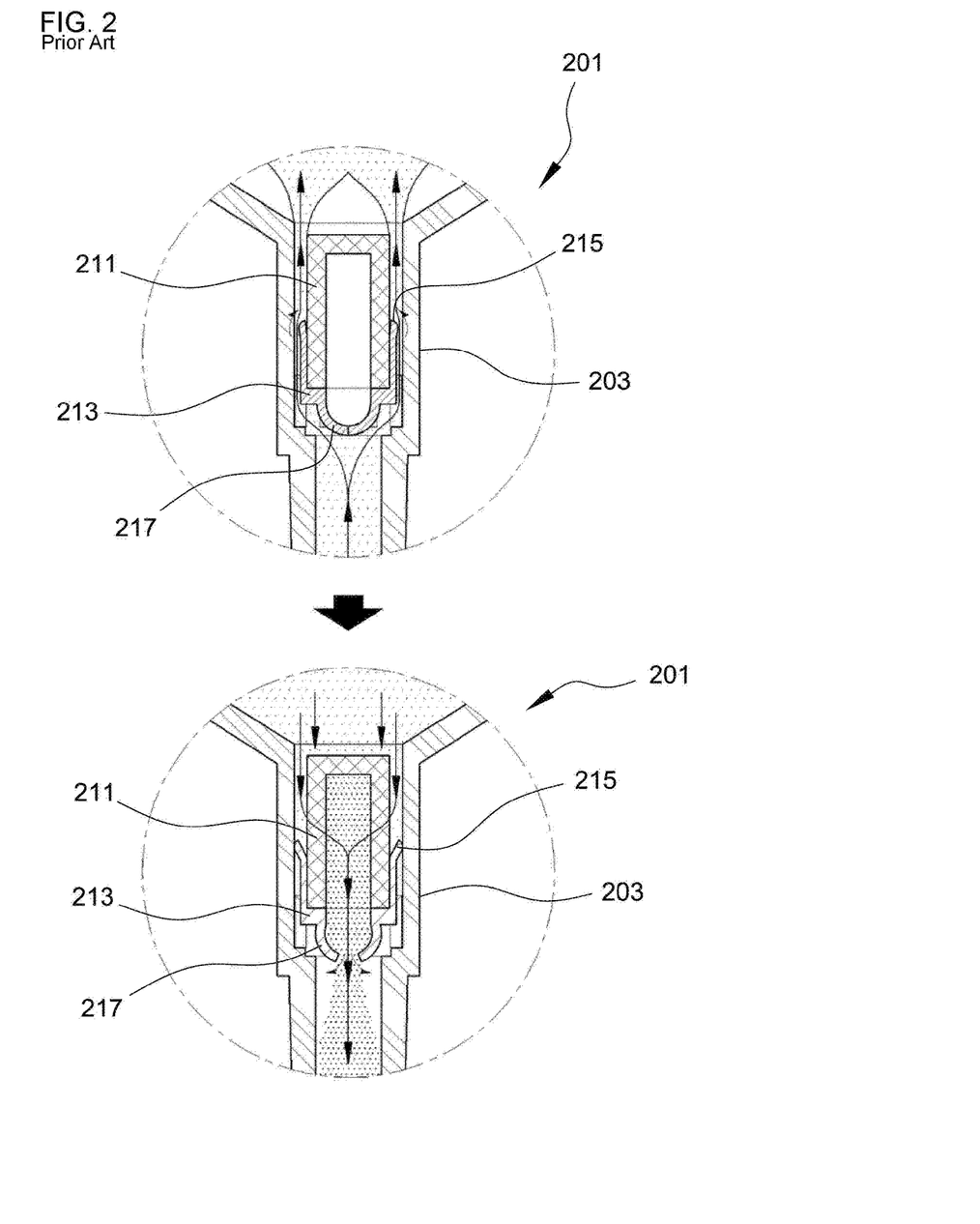
FIG. 2 is a partially enlarged view illustrating a filter syringe of the related art.

A filter syringe, which is generally indicated by a reference numeral 201 in FIG. 2, includes a filter 211 and a check valve 213 which are mounted in an end of a barrel 203 (e.g., Korean Patent No. 10-1354451). As can be seen from the upper portion in FIG. 2, when the liquid is withdrawn into the syringe from the drug container, a gap between the barrel 203 and an inner end of the check valve 213 becomes wide, so that the syringe aspirates the liquid with the foreign substances in the arrow direction. Meanwhile, as can be seen from the lower portion in FIG. 2, when the liquid is administrated into a body by use of the syringe, the inner end 215 of the check valve 213 comes into contact with the inner peripheral surface of the barrel 203, and an outer end 217 of the check valve 213 is opened to allow the liquid to flow in the arrow direction. in this instance, the foreign substances contained in the liquid are filtered by the filter 211.

When the filter syringe 201 injects the liquid, the foreign substances contained in the liquid are filtered by the filter 211, but since the complicated check valve 213 and the filter are used, the cost is increased.

As can be seen from the upper portion in FIG. 2, after the syringe aspirates the liquid and then the injection needle is removed from the drug container, the injection needle is exposed in air until the injection needle is inserted into the body. Therefore, there is a problem in that possibility of air infection or contact infection is high, thereby deteriorating performance of health control.

Figure 3:
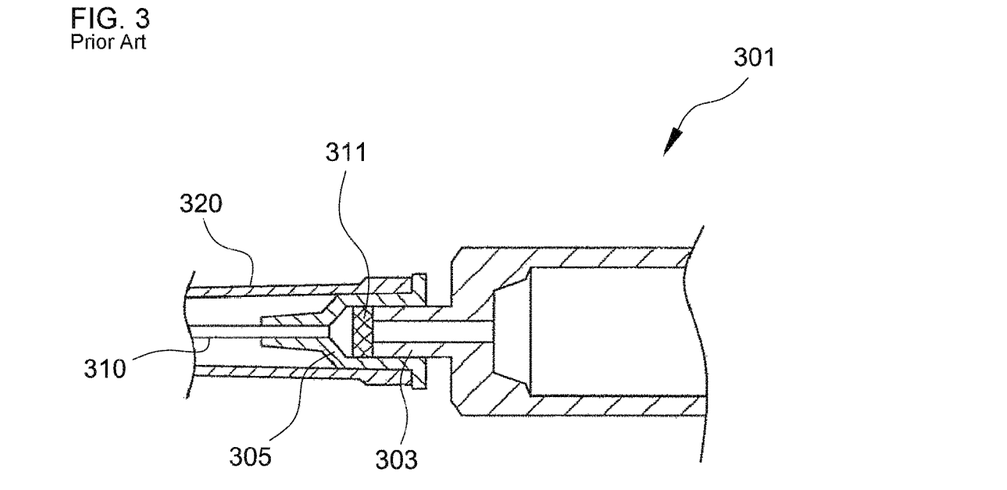
FIG. 3 is a partially enlarged view illustrating a filter syringe having a basic shape according to the related art.

In addition, a basic filter syringe employing the filter disclosed in the above patents, which is generally indicated by a reference numeral 301, includes a filter 311 interposed between a barrel 303 and an injection needle hub 305, that is, mounted in the injection needle hub 305 so that the filter is positioned at a front end of the barrel 303. When a protective cap 320 is removed and then an injection needle 310 is inserted into a drug container to aspirate a liquid into the syringe, foreign substances contained in the liquid are filtered by the filter 311, so that only the liquid is withdrawn into the syringe. After that, when the liquid is injected, the injection needle 310 used for infusion is discarded, and a new injection needle is used, which can perform safe injection.

In this instance, since two injection needles are used for once injection, treatment costs are increased, and it brings waste of resources.

SUMMARY OF THE INVENTION

Accordingly, the present invention has been made in view of the above problems inherent in syringes of the related art, and an object of the present invention is to provide a syringe including a needle for infusing a liquid and a needle for injecting the liquid, separately, to more stably protect the injection needle, without providing an additional protective component.

Another object of the present invention is to provide a syringe, of which an injection needle shaft and an infusion needle shaft are separately disposed not to be overlapped with each other, so that the infusion needle shaft can be made to have a small diameter, thereby increasing an insertion force of the injection needle shaft and thus improving performance and convenience in use of the syringe.

A further object of the present invention is to improve a fastening force of an injection needle to a cylinder by simplifying and diversifying a method and component for fastening an injection needle shaft and an infusion needle shaft.

A still further object of the present invention is to minimize an externally exposed time of an injection needle shaft, thereby preventing a syringe from being infected, for example, hospital acquired infection, and thus increasing safety of injection treatment.

A still further object of the present invention is to simplify a filtering structure of an injection needle, thereby lowering a cost of the injection needle, reducing a cost required for injection, and to reduce the number of needles to be wasted after use, thereby lowering all costs required for a syringe.

Technical Solution

To accomplish the above-mentioned object, according to a first aspect of the present invention, there is provided a dual-needle syringe capable of preventing infection, the dual-needle syringe including: an infusion needle shaft configured to aspirate a liquid from a drug container, with a sharp point of one end being inserted into the drug container, in which the liquid flows from one end to the other end; an injection needle shaft having a sharp point of one end inserted into a body, and the other end connected to the syringe, through which the liquid filled in the syringe is injected into a body; a hub barrel configured to connect the other end of the infusion needle shaft and the other end of the injection needle shaft, and engaged to a barrel of the syringe to infuse the liquid, which is aspirated from the drug container through the infusion needle shaft, into the syringe through the injection needle shaft, the hub barrel having an infusion needle shaft hub and an injection needle shaft hub which can be separated from each other before the liquid is injected; and a filter which is mounted in the hub barrel at a position close to the infusion needle shaft on the basis of a portion to be separated to filter foreign substances contained in the liquid which is aspirated from the drug container.

Preferably, the hub barrel is formed as a single piece so that the hub barrel can be divided into the infusion needle shaft hub and the injection needle shaft hub before the liquid is injected.

Preferably, the hub barrel is formed so that the infusion needle shaft hub and the injection needle shaft hub can be detachably engaged to each other before the liquid is injected.

Preferably, an auxiliary filter is mounted in the hub barrel at a position close to the injection needle shaft on the basis of a score line of the hub barrel, thereby removing foreign substances remaining in an inner peripheral surface of the injection needle shaft hub of the hub barrel which is separated when the liquid is injected, to prevent the foreign substances from passing the injection needle shaft.

With the dual-needle syringe capable of preventing infection according to the present invention, since the needle for infusing the liquid and the needle for injecting the liquid, that is, the infusion needle shaft and the injection needle shaft, are disposed opposite to each other, it is possible to minimize the diameter of the infusion needle shaft. Therefore, the operation of inserting the infusion needle shaft into the lid of the drug container can be easily performed, thereby remarkably improving the user convenience of the syringe.

Also, since the infusion needle shaft and the injection needle shaft are disposed opposite to each other, as described above, the injection needle shaft can be positioned in the cylinder prior to use, thereby safely and cleanly protecting and keeping the injection needle shaft from air infection or contact infection.

In addition, since the infusion needle shaft and the injection needle shaft are respectively provided with the filter, it is possible to remove the foreign substances contained in the liquid when the drug is withdrawn from the drug container through the infusion needle shaft and the liquid filled in the cylinder is injected into the body, thereby further improving the filtering performance against the foreign substances.

Furthermore, in spite of the filtering performance, the internal structure of the syringe needle is simple, thereby lowering the cost of the needle. The injection treatment can be performed at a low cost, without using an additional needle, thereby lowering all costs required for the syringe.

DETAILED DESCRIPTION OF THE INVENTION

Hereinafter, a dual-needle syringe according to a preferred embodiment of the present invention will be in detail given with reference to the attached drawings.

The dual-needle syringe according to the embodiment of the present invention generally includes an infusion needle shaft 3, an injection needle shaft 5, a hub barrel 7, and a filter 9.

Figure 4:
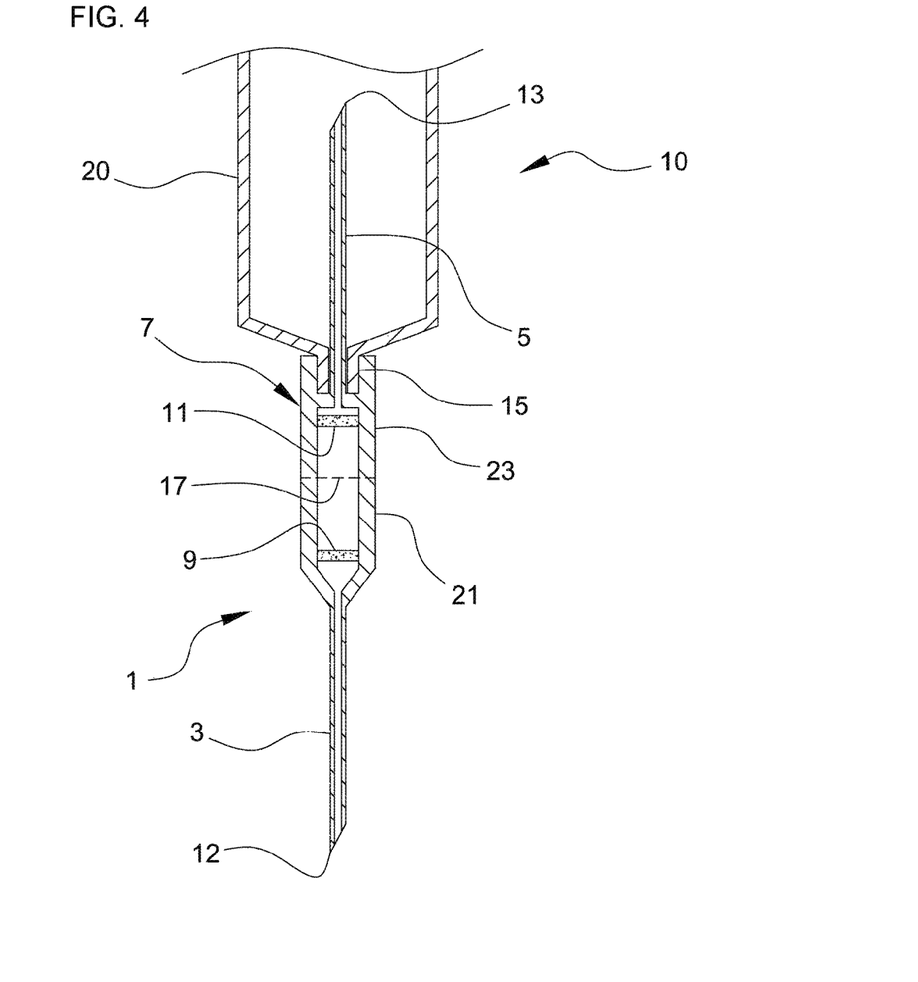
FIG. 4 is a cross-sectional view illustrating a dual-needle syringe capable of preventing infection according to the present invention.
Figure 5:
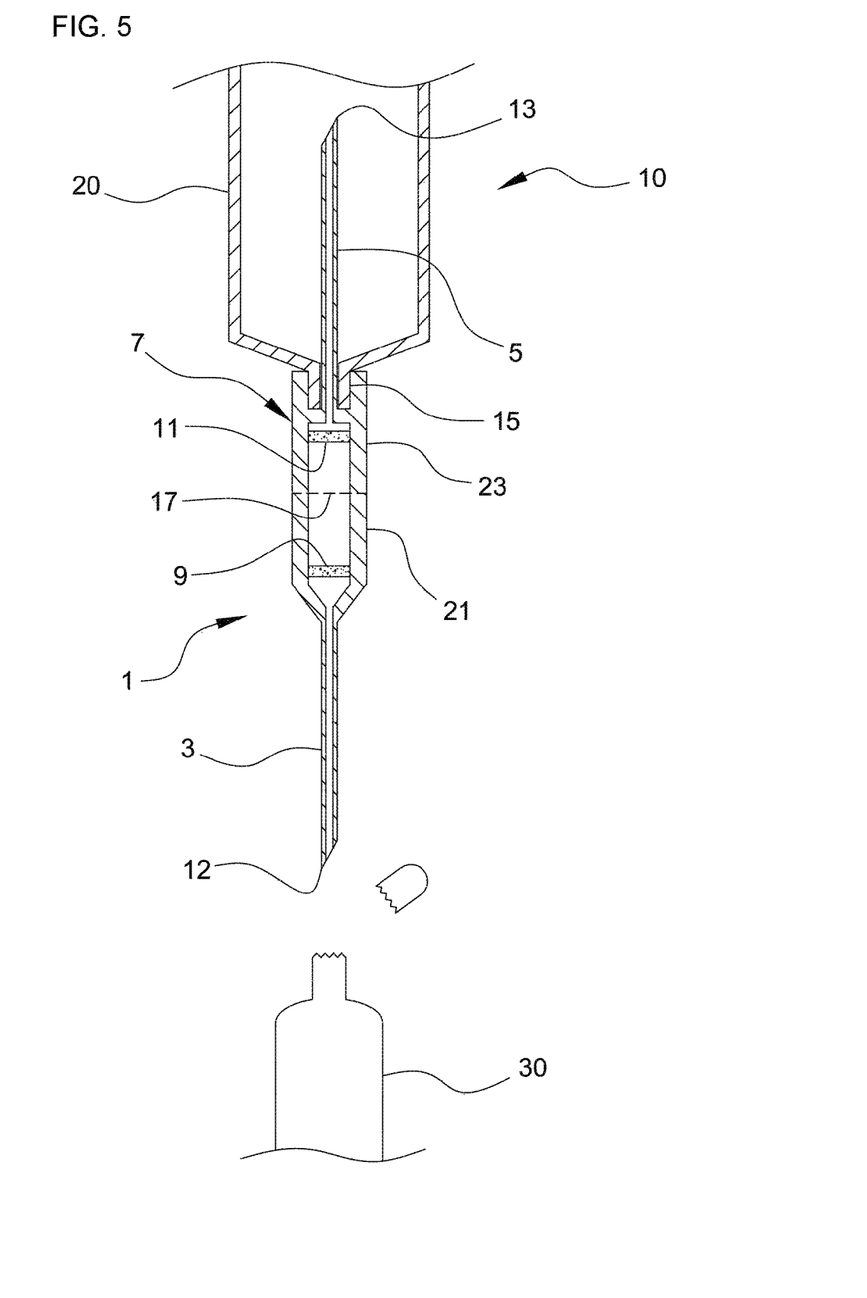
FIG. 5 is a view illustrating a state before an injection needle shaft is inserted into an ampoule.
Figure 6:
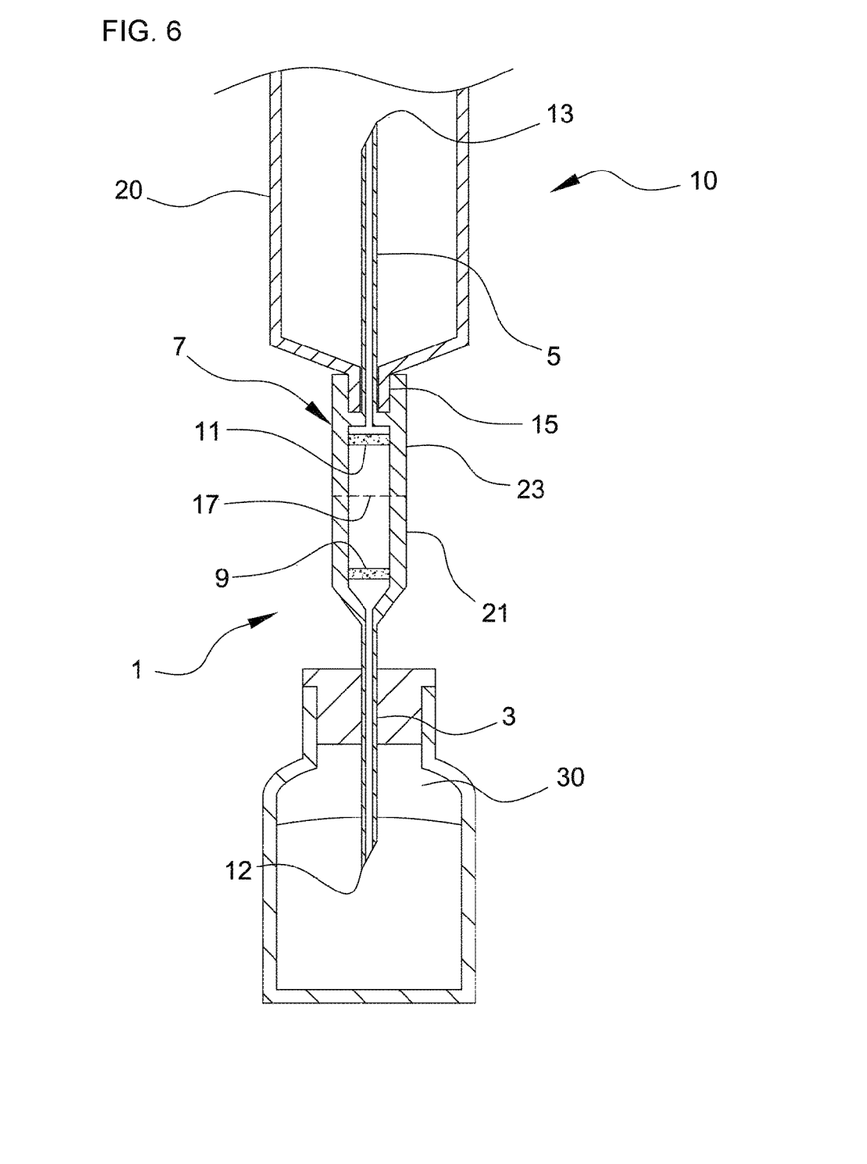
FIG. 6 is a view illustrating a state before an injection needle shaft is inserted into a vial.

First, the infusion needle shaft 3 is configured to aspirate a liquid into a cylinder 20 of a syringe 10, as illustrated in FIG. 4, and has a tubular body to form a liquid passage therein, like a general injection needle, of which one end is extended and connected to the hub barrel 7, and the other end is provided with a sharp point to be easily inserted into a drug container 30 to aspirate the liquid, as illustrated in FIG. 6. In other words, the injection needle shaft 5 is not required for the sharp point 12 in case where an ampoule is used as the drug container 30, as illustrated in FIG. 5, but should be provided with the shaft point 12 in case a vial is used as the drug container 30, as illustrated in FIG. 6.

Figure 9:
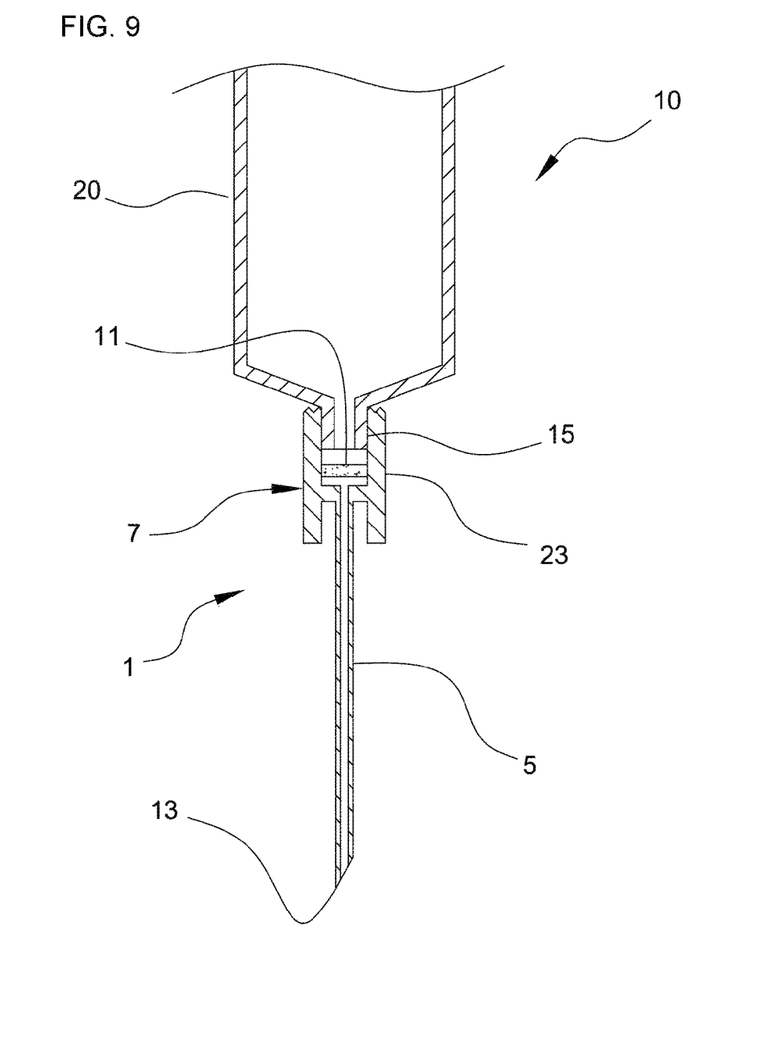
FIG. 9 is a view a state after an injection needle shaft hub is fitted into a barrel.

The injection needle shaft 5 corresponds to an injection needle of a general syringe which is inserted into a body to inject a liquid thereto. As illustrated in FIG. 4, the injection needle shaft 5 has an extended tubular body to form a liquid passage therein, of which one end is provided with a sharp point to be inserted into the body, and the other end is connected to the hub barrel 7. Before the injection needle shaft 5 is used for injection, the injection needle shaft is maintained in a state of being inserted into the cylinder 20 by the hub barrel 7, as illustrated in FIG. 4, but when it is used to inject the liquid, the injection needle shaft is extended from a front end of the cylinder 20 by the hub barrel 7, as illustrated in FIG. 9.

The hub barrel 7 is configured to connect the infusion needle shaft 3 and the injection needle shaft 5 prior to injection, and as illustrated in FIG. 4, is detachably mounted to the barrel 15 of the cylinder 20. In this instance, the shaft point of the injection needle shaft 5 should be inserted into the barrel 15, so that the injection needle shaft 5 is protected within the cylinder 20 prior to injection. Accordingly, before the syringe is infused with the liquid, the hub barrel 7 guides the flow of the liquid from the drug container 30 to the cylinder 20 through the infusion needle shaft 3.

Figure 7:
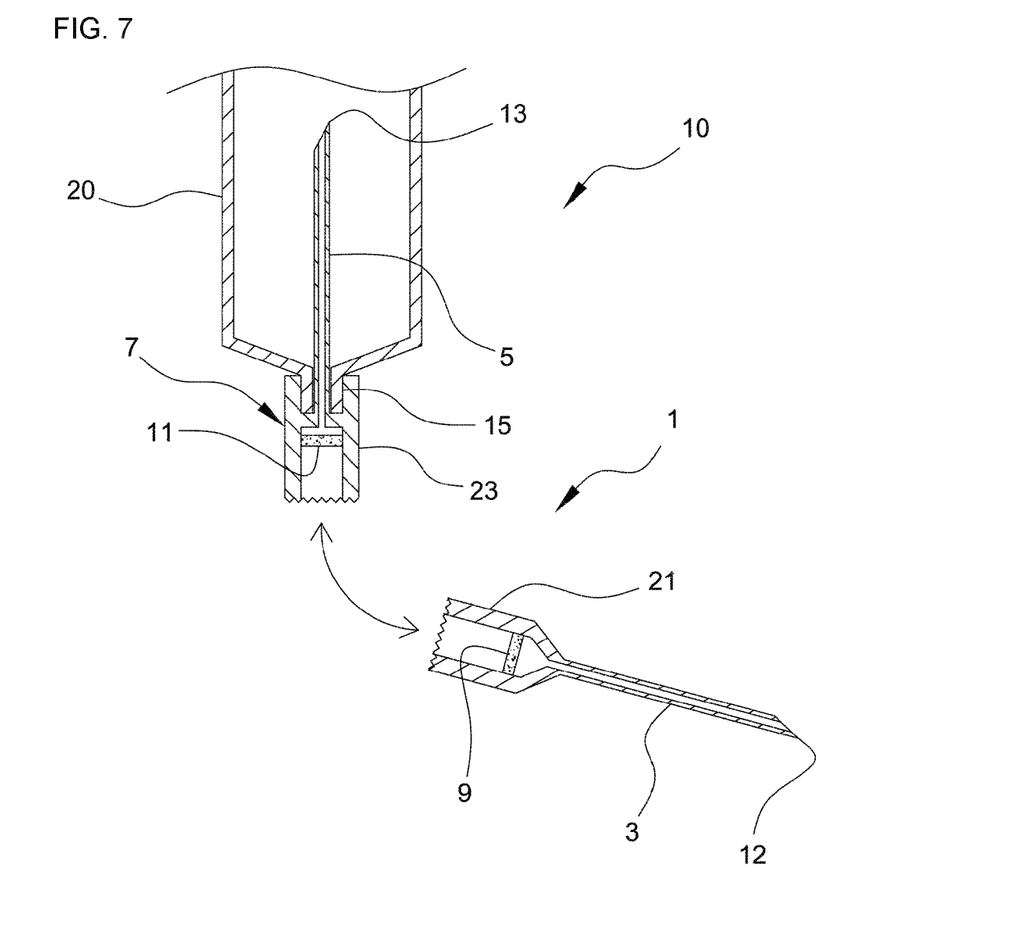
FIG. 7 is a view illustrating a state in which a hub barrel is broken to form an injection needle shaft hub and an infusion needle shaft hub.
Figure 8:
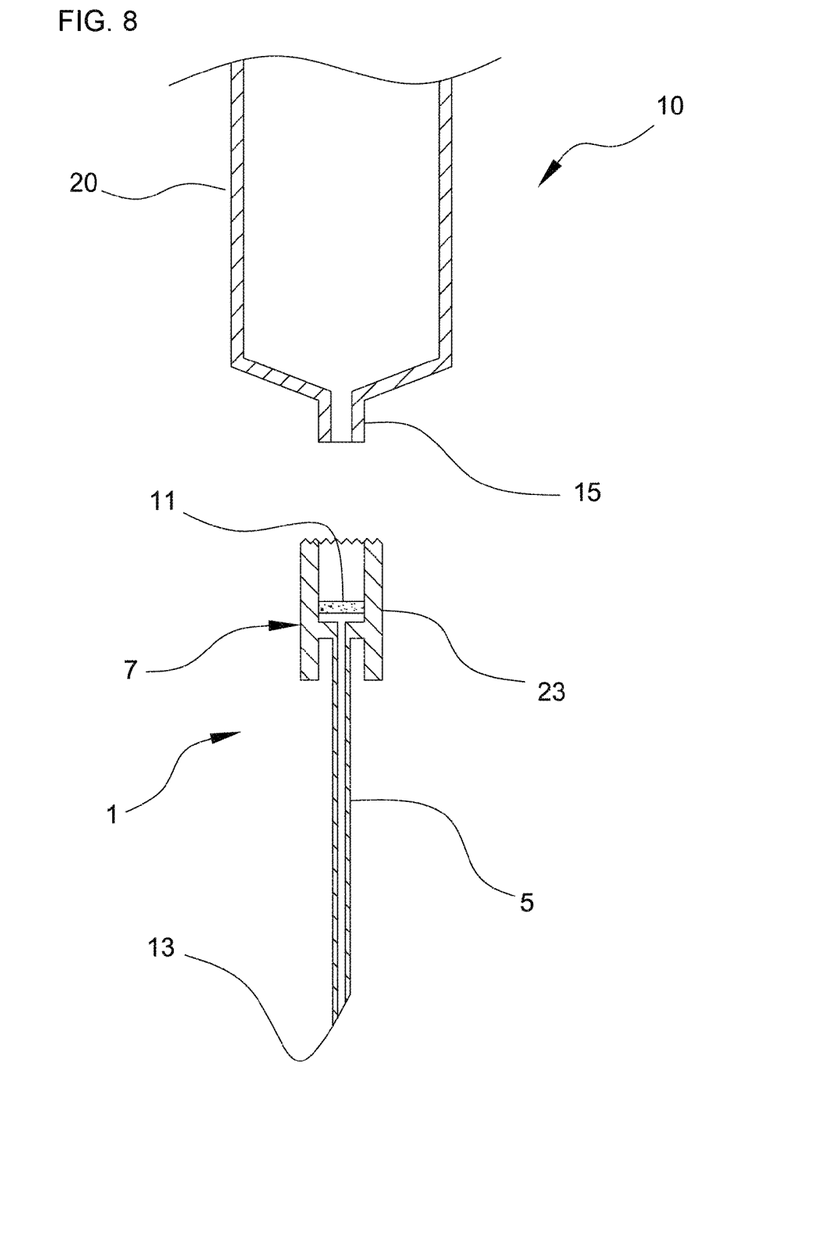
FIG. 8 is a view a state before an injection needle shaft hub is fitted into a barrel.

When the liquid is withdrawn from the drug container, the hub barrel 7 is broken along a scored line 17 to form an infusion needle shaft hub 21 and an injection needle shaft hub 23. As illustrated in FIGS. 8 and 9, the injection needle shaft hub 23 is engaged to the barrel 15, so that when the injection needle shaft 5 is inserted into the body, the liquid is injected into the body from the cylinder 20 through the injection needle shaft 5. In this instance, the hub barrel 7 may be formed to be broken in various methods. One example of the breaking methods is illustrated in FIG. 7, in which the hub barrel 7 is broken by an external force to form the infusion needle shaft hub 21 and the injection needle shaft hub 23. In this instance, the hub barrel 7 is broken along the score line 17, and, to this end, the score line 17 is formed to be easily broken.

As another breaking method of the hub barrel 7, although not illustrated, the infusion needle shaft hub 21 and the injection needle shaft hub 23 may be detachably engaged to each other by a screw or the like. In other words, an inner peripheral surface of the injection needle shaft hub 23 is provided with a female threaded portion, while an outer peripheral surface of the infusion needle shaft hub 21 is provided with a male threaded portion, so that the infusion needle shaft hub 21 and the injection needle shaft hub 23 can be detachably engaged to each other by thread engagement.

The filter 9 is a means for filtering foreign substances contained in the liquid when the liquid is aspirated through the infusion needle shaft 3. As illustrated in FIG. 4, the filter 9 is mounted in the hub barrel 7 at a position close to the infusion needle shaft 3 on the basis of the score line 17 of the hub barrel 7, that is, on the side of the infusion needle shaft hub 21. As illustrated in FIG. 5 or 6, when the liquid is withdrawn into the syringe 10 through the infusion needle shaft 3, the filter 9 filters various foreign substances which remain in the drug container 30 and are withdrawn into the hub barrel 7 together with the liquid.

The hub barrel 7 is provided with the filter 9, and is preferably provided with an auxiliary filter 11, as illustrated in FIG. 4. The auxiliary filter 11 removes foreign substances remaining in the injection needle shaft hub 23 to prevent the foreign substances from flowing into the injection needle shaft 5, when the liquid is injected into the body through the injection needle shaft 5. In other words, even though foreign substances generated when the hub barrel 7 is broken to inject the liquid remain in the injection needle shaft hub 23 after a desired quantity of liquid is withdrawn into the cylinder 20, the auxiliary filter 11 removes all foreign substances contained in the liquid while the liquid moves from the injection needle shaft hub 23 to the injection needle shaft 5 at injection. To this end, as illustrated in FIG. 4, the auxiliary filter 11 is mounted in the hub barrel 7 at a position close to the injection needle shaft 5 on the basis of the score line 17 of the hub barrel 7, that is, on the side of the injection needle shaft hub 23.

Now, the operation of the duel-needle syringe capable of preventing the infection according to the preferred embodiment of the present invention will be described.

In order to inject the liquid into the body by the duel-needle syringe capable of preventing the infection according to the preferred embodiment of the present invention, as illustrated in FIG. 5 or 6, the infusion needle shaft 3 is inserted into the drug container 30, such as an ampoule or a vial. In this instance, since the ampoule is opened by snapping an upper neck thereof, as illustrated in FIG. 5, debris enters into the liquid at breaking. In case of the vial, when the sharp point 13 of the injection needle shaft 5 penetrates a rubber lid, the inside of the sharp point 13 is caught by rubber debris.

If a plunger (not illustrated) is pulled from the cylinder 20 in the state in which the injection needle shaft 5 is inserted into the drug container 30, the liquid filled in the drug container 30 is withdrawn from the infusion needle shaft 3 to the barrel 20 through the hub barrel 7 and the injection needle shaft 5. In this instance, the foreign substances floating in the ampoule or caught by the sharp point 12 of the infusion needle shaft 3 are removed by the filter 9.

If all liquid is withdrawn from the drug container 30 to the cylinder 20, as illustrated in FIG. 7, the hub barrel 7 is broken along the score line 17. In this instance, in case where the hub barrel 7 is formed as one piece, as illustrated in the drawings, the hub barrel is divided into the infusion needle shaft hub 21 and the injection needle shaft hub 23 along the score line 17. Although not illustrated, in case where the infusion needle shaft hub is threadedly engaged with the injection needle shaft hub, the threaded engagement is released along the score line 17. However, in the process of breaking the hub barrel 7, various foreign substances, such as ampoule debris, generated when the hub barrel 7 is broken remain in the injection needle shaft hub 23.

As illustrated in FIG. 8, a user pulls the injection needle shaft hub 23 from the barrel 15, reverses the direction of the injection needle shaft 5 and the injection needle shaft hub 23, and then engages the injection needle shaft hub 23 to the barrel 15. In this instance, since the injection needle shaft 5 exposed in the air is kept in the syringe for a long time after infusion of the liquid, it can be safely and hygienically used, without worrying about air infection or contact infection which is caused by long-term exposure.

If preparation for the injection is completed by the above process, the user inserts the injection needle shaft 5 into the body, such as a patient's skin, by holding the cylinder 20. And then, if the user pushes the plunger into the barrel 20, the liquid filled in the barrel 20 is injected into the body through the injection needle shaft 5. In this instance, various foreign substances remaining in the injection needle shaft hub 23 are removed by the auxiliary filter 11. Accordingly, the process of infusing the liquid by the dual-needle syringe 1 capable of preventing infection, that is, the injection operation, is completed.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

With the dual-needle syringe capable of preventing infection according to the present invention, since the needle for infusing the liquid and the needle for injecting the liquid, that is, the infusion needle shaft and the injection needle shaft, are disposed opposite to each other, the diameter of the infusion needle shaft can be minimized, so that it is possible to easily perform the insertion operation when the infusion needle shaft is inserted into the lid of the drug container. Therefore, the use convenience of the syringe can be remarkably improved.

The invention claimed is:

1. A dual-needle syringe capable of preventing infection, the dual-needle syringe comprising:

a cylinder (20) releasably connected to one of two ends of a hub barrel (7);

the hub barrel (7) connected at its other end to an infusion needle shaft (3);

the infusion needle shaft (3) having a sharp point (12) opposite to its connection to the hub barrel (7) with the sharp point (12) for insertion into a container (30) to aspirate a liquid from the container (30) through the infusion needle shaft into the hub barrel (7);

an injection needle shaft (5) having an end disposed near and within the end of the hub barrel (7) releasably connected to the cylinder (20), the injection needle shaft (5) extending from its end disposed near and within the end of the hub barrel (7) into the cylinder (20), the injection needle shaft (5) ending in a sharp point (13) and being removably disposed within the cylinder (20), and the injection needle shaft (5) passing the liquid in the hub barrel (7) through the injection needle shaft (5) into the cylinder (20);

the hub barrel (7) being formed to divide into an infusion needle shaft hub (21) connected to the infusion needle shaft (30) and an injection needle shaft hub (23) connected to the injection needle shaft (5); and the injection needle shaft hub (23) with the injection needle shaft (5) being detachable from the cylinder (20) to remove the injection needle shaft (5) from the cylinder, and the injection needle shaft hub (23), after division from the infusion needle shaft hub (21), being re-attachable to the cylinder (20) by connecting the end of the injection needle shaft hub (23) formerly connected to the infusion needle shaft hub (21) to the cylinder (20), whereby the infusion needle shaft (3) aspirates the liquid from the container (30) into the hub barrel (7) from which the injection needle shaft (5) transfers the liquid into the cylinder (20), after the transfer of the liquid into the cylinder (20), the hub barrel (7) divides into the infusion needle shaft hub (21) with the infusion needle shaft (3) and the injection needle shaft hub with the injection needle shaft (5), and after the division, the injection needle shaft hub (23) with the injection needle shaft (5) is detachable from the cylinder (20) so the injection needle shaft hub (23) with the injection needle shaft (5) is re-attachable to the cylinder (20) with the injection needle shaft (5) protruding from the cylinder (20) for use in injecting the liquid in the cylinder (20).

* * * * *